(12) United States Patent
Kuzma et al.

(10) Patent No.: US 6,361,797 B1
(45) Date of Patent: Mar. 26, 2002

(54) HYDROGEL COMPOSITIONS USEFUL FOR THE SUSTAINED RELEASE OF MACROMOLECULES AND METHODS OF MAKING SAME

(75) Inventors: Petr Kuzma, Princeton, NJ (US); Harry Quandt, Bensalem, PA (US)

(73) Assignee: Hydro Med Sciences, Inc., Wilmington, DE (US)

( * ) Notice: Subject to any disclaimer, the term of this patent is extended or adjusted under 35 U.S.C. 154(b) by 0 days.

(21) Appl. No.: 09/646,066

(22) PCT Filed: Jan. 26, 2000

(86) PCT No.: PCT/US00/01664
§ 371 Date: Dec. 7, 2000
§ 102(e) Date: Dec. 7, 2000

(87) PCT Pub. No.: WO00/44356
PCT Pub. Date: Aug. 3, 2000

Related U.S. Application Data
(60) Provisional application No. 60/117,546, filed on Jan. 28, 1999.

(51) Int. Cl.[7] .............................. A61K 9/14; A61K 9/24; A61F 13/00; A61F 2/00
(52) U.S. Cl. ....................... 424/486; 424/422; 424/423; 424/473
(58) Field of Search ................................. 424/486, 422, 424/419, 481, 423, 473

(56) References Cited

U.S. PATENT DOCUMENTS

| | | | |
|---|---|---|---|
| 4,954,587 A | | 9/1990 | Mueller |
| 4,959,217 A | | 9/1990 | Sanders et al. |
| 5,266,325 A | * | 11/1993 | Kuzma et al. ............... 424/422 |
| 5,292,515 A | * | 3/1994 | Moro et al. .................. 424/422 |
| 5,431,921 A | | 7/1995 | Thombre |

* cited by examiner

Primary Examiner—Thurman K. Page
Assistant Examiner—Blessing Fubara
(74) Attorney, Agent, or Firm—Howson and Howson

(57) ABSTRACT

A method of producing a homogenous porous hydrogel useful for drug delivery is described. The pores of the hydrogel are created by diffusion enhancers to facilitate sustained delivery of macromolecules. Also described are various articles produced from these hydrogels.

26 Claims, 2 Drawing Sheets

HYDROGEL COMPOSITIONS USEFUL FOR THE SUSTAINED RELEASE OF MACROMOLECULES AND METHODS OF MAKING SAME

CROSS-REFERENCE TO RELATED APPLICATIONS

This is a 371 of PCT/US00/01664, which claims the benefit of the priority of U.S. Patent Application No. 60/117,546, filed Jan. 28, 1999.

FIELD OF THE INVENTION

The invention relates generally to the controlled release of macromolecules, and particularly, to the preparation of a copolymer useful in release of such macromolecules.

BACKGROUND OF THE INVENTION

The sustained release of active agents is known to be of value. In particular, long-term drug delivery has been shown to be effective in obtaining constant serum levels and in improving patient compliance.

It is well known in the art that hydrogel membranes may be used for sustained delivery of active compounds. There are several theories regarding the mechanism of solute diffusion in hydrogels. Lee et al., *J. Polymer Science: Polymer Symposium*, 66:227–237 (1979) hypothesized that there are three classes of water in hydrogels, including, "Z" water which is bound to the polymer matrix, "Y" water which is partially affected by the polymer matrix, and bulk or "X" water which is unaffected by the polymer matrix. Kim et al., *ACS Symp. Ser.*, 127:347–359 (1980) expanded upon the Lee model. Kim et al, concluded that the diffusion of hydrophilic solutes through hydrogel membranes depends on molecular size of the solute and water content of the hydrogel and that the permeation takes place via the bulk water.

The hydrogels which have been described in the art have some porosity, due to the network structure of the crosslinked polymer chains, which allow smaller molecules to diffuse through the structure. The size of the pores varies depending upon the hydrogel chemical composition and thus, its degree of hydration (equilibrium water content, "EWC"). However, the hydrogels described in the art are not particularly well adapted to delivery of large molecules (macromolecules).

What is needed in the art are compositions which are well suited for sustained delivery of macromolecules and methods for producing these compositions.

SUMMARY OF THE INVENTION

In a first aspect, the present invention provides a method for preparing a homogenous porous hydrogel which permits sustained delivery of macromolecules. The method involves mixing about 60 weight percent to about 95 weight percent comonomers, at least one of which is hydrophilic, and sufficient amounts of a crosslinker and a liquid diffusion enhancer which is miscible with the comonomers, to yield a homogenous copolymer hydrogel having the equilibrium water content (EWC) value in the range from about 20% to about 85%. The methods and compositions of the invention are particularly well suited to rotational casting of the hydrogel into the form of a cartridge, which preferably has walls of uniform thickness which define a reservoir. The hydrogel of the invention is useful for sustained release of macromolecular compounds having a molecular weight of up to 100,000.

In a preferred embodiment, the polymerizable liquid mixture contains about 1 weight percent to about 50 weight percent diffusion enhancer which may be readily selected from among C1–C4 alkyl alcohol, allyl alcohol, tetrahydrofurfuryl alcohol, cyclohexyl alcohol, diethylene glycol, polyethylene glycols, glycerol, acetone, ethylene glycol monomethyl ether, ethylene glycol monoethyl ether, glyceryl isopropylidene ether dioxane, tetrahydrofuran; ethyl acetate; dimethyl sulfoxide; water, and mixtures thereof.

In another aspect, the invention provides an article produced according to the method of the invention.

In yet another aspect, the invention provides a method for the preparation of a delivery device for the sustained release of an active agent. This method involves introducing an active agent, and optionally, a pharmaceutically acceptable carrier, into the reservoir of a cartridge prepared according to the invention. Subsequently, at least one polymerizable liquid monomer is added into the upper portion of the reservoir and is then polymerized to seal the opening of the reservoir with a plug of water-swellable, water-insoluble polymer to form a delivery device which provides a predetermined release of the active agent.

In still another aspect, the invention provides a delivery device prepared according to the method above.

Other aspects and advantages of the invention will be readily apparent from the detailed description of the invention.

DETAILED DESCRIPTION OF THE INVENTION

Figure 1:
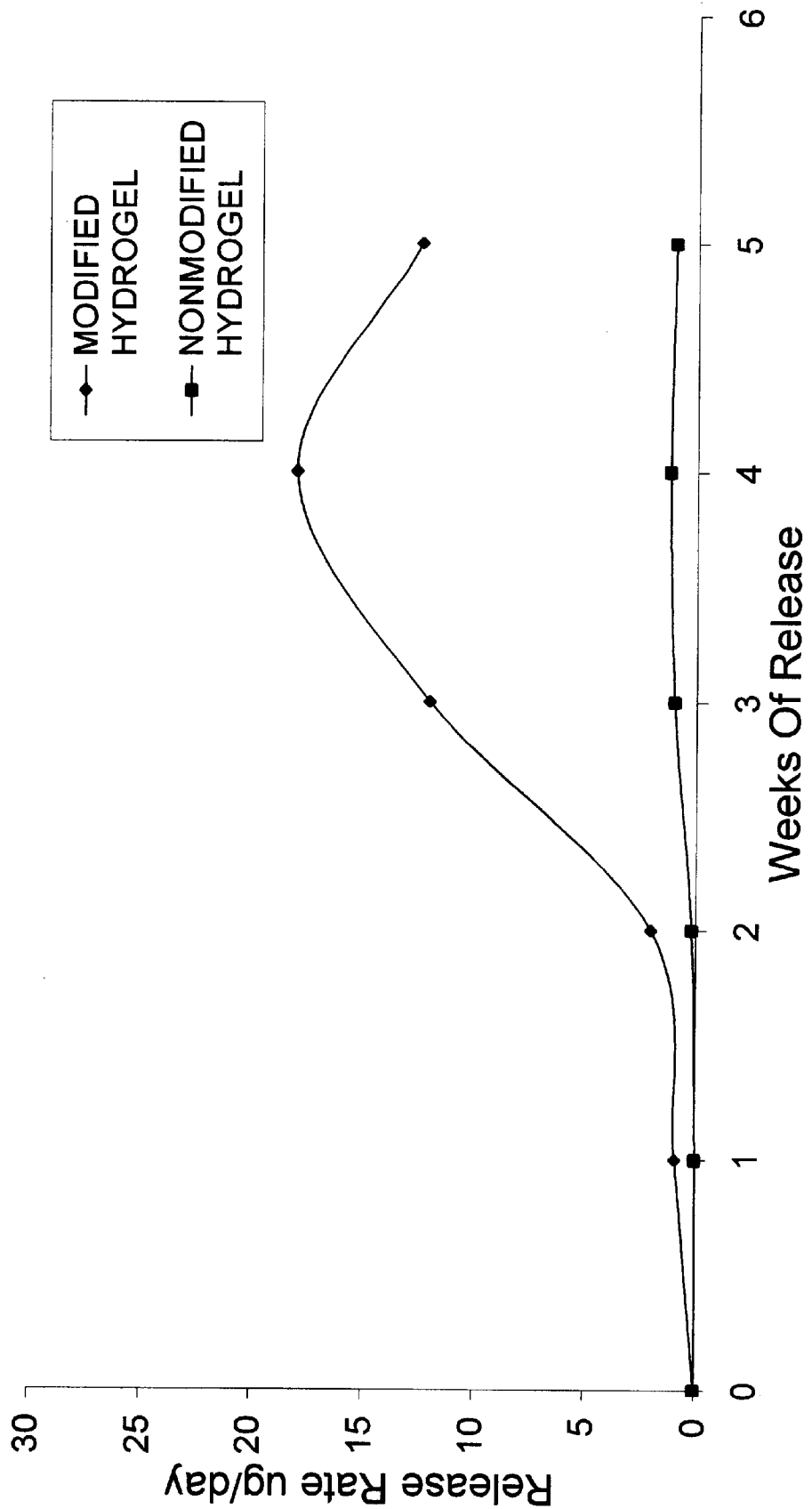
FIG. 1 illustrates the rate of release of lysozyme from a hydrogel delivery device prepared as described in Example 9 of the invention (modified hydrogel), as compared to a hydrogel delivery device prepared according to convention methods (non-modified hydrogel).
Figure 2:
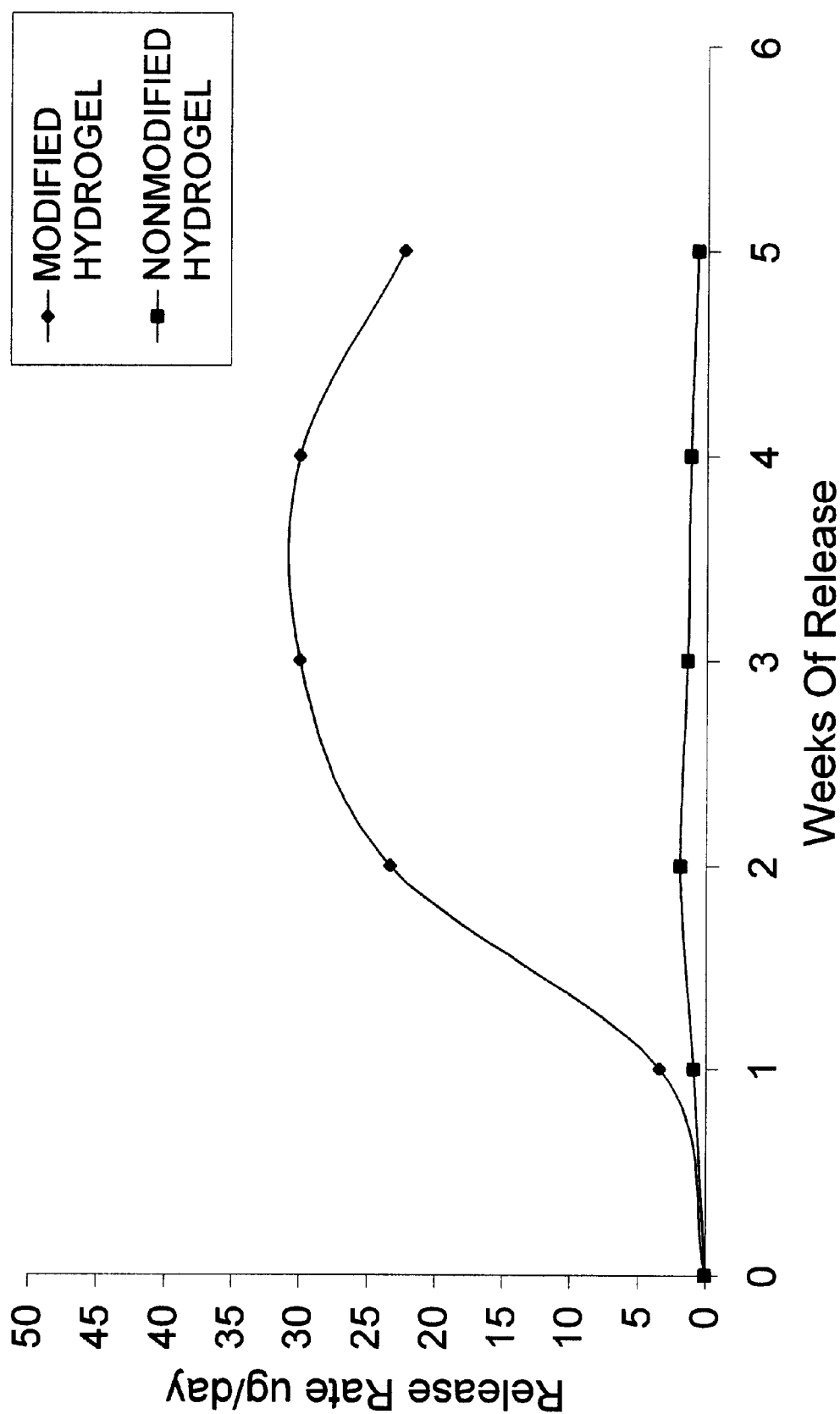
FIG. 2 illustrates the rate of release of lysozyme from a hydrogel delivery device prepared as described in Example 12 of the invention (modified hydrogel), as compared to a hydrogel delivery device prepared according to convention methods (non-modified hydrogel).

The present invention provides methods of producing homogenous porous hydrogels which are well suited to delivery of large molecules. These hydrogels may be readily formed into delivery devices which provide sustained delivery of macromolecular drugs and other active agents. While the methods and compositions of the invention have been found to be particularly well suited to production of hydrogel delivery devices produced using spin casting techniques, the methods of the invention may be readily utilized in other production methods.

As described herein, the inventor has found that the inclusion of certain liquid diffusion enhancers (which remain in liquid form following polymerization) in the mixture of polymerizable materials, permits the creation of a hydrogel having pores which are evenly dispersed and of a size to enhance diffusion of larger molecules through the network structure of the crosslinked polymer chains of the hydrogel. Additional characteristics and advantages of these liquid diffusion enhancers are described herein.

This invention may be especially useful in cases where the compounds, such as proteins, are "pegylated", as this process will significantly increase the original molecular weight by the polyethylene glycol (PEG) portion. As used herein, "pegylation" refers to the practice of adding PEG to a peptide, protein, or other active agent. This practice, well known in the art, has been found to stabilize proteins or peptides, by decreasing their recognition by the immune system, and improving their half-life (by slowing their clearance by) in the body.

The expression "active agent" as used herein includes any compound or mixture thereof that can be delivered from the delivery device to produce a useful result. The active agents whether in solid or liquid form will have sufficient solubility or miscibility in an aqueous system to render them capable of being released through the hydrogel membranes of the invention into the delivery environment. These active agents include drugs and macromolecules as used herein. Suitably, the active agents may be included in a single large pore, i.e., a "revervoir"-type delivery device, or may be included in a multiplicity of pores which are defined by the hydrogel of the invention.

"Drugs" include any physiologically or pharmacologically active substance that produces a localized or a systemic effect in animals. The drugs that can be delivered include inorganic and organic drugs that act on the central nervous system, psychic energizers, tranquilizers, anti-convulsants, muscle relaxants, anti-parkinson, analgesic, anti-inflammatory, anesthetic, antispasmodic, muscle contractants, anti-microbials, anti-malarials, hormonal agents, sympathomimetic, cardiovascular, diuretics, anti-parasitic and the like.

The expression "macromolecule" as used herein is intended to include compounds having a molecular weight in the range of about 10,000 to about 250,000, and those having molecular weights in the range of 50,000 to 200,000, as well as those having molecule weights in the range of 100,000 to 150,000.

The Components of the Reaction Mixture

It is currently preferred for the materials which are utilized in the reaction mixture, including the monomers, co-monomers, diffusion enhancers, and the like, to be biologically compatible. That is, these materials are preferably biologically inert, i.e., have no significant effect on animals, or the human body. In particularly preferred embodiments, the materials have previously been approved for use in animals by the USDA and/or for use in humans by the FDA, or equivalent agencies. However, such prior regulatory approval is not a requirement. It is well within the skill of those in the art to select suitable materials, including those which are described below.

Polymerizable material useful in the manufacture of the novel homogenous porous hydrogels of the invention include a wide variety of hydrophilic, ethylenically unsaturated compounds, in particular, hydrophilic monomers such as the monoester of an acrylic acid (e.g., methacrylic acid) with a polyhydroxy compound having an esterifiable hydroxyl group and at least one additional hydroxyl group such as the monoalkylene and polyalkylene polyols of methacrylic acid and acrylic acid, e.g., 2-hydroxyethyl methacrylate and acrylate, diethylene glycol methacrylate and acrylate, propylene glycol methacrylate and acrylate, dipropylene glycol methacrylate and acrylate, glycidyl methacrylate and acrylate, glyceryl methacrylate and acrylate, and the like; the 2-alkenamides, e.g., acrylamide, methacrylamide, and the like; the N-alkyl and N,N'-dialkyl substituted acryl-amides and methacrylamides such as N-methylmethacrylamide, N,N'-dimethylmethacrylamide, and the like; N-vinylpyrrolidone; the alkyl-substituted N-vinylpyrrolidones, e.g., methyl substituted N-vinylpyrrolidone; N-vinylcaprolactam; the alkyl-substituted N-vinylcaprolactam, e.g., N-vinyl-2-methylcaprolactam, N-vinyl-3,5-dimethylcaprolactam, and the like. Other suitable monomers include those described in U.S. Pat. No. 4,303,066 (line 36), et seq. In one desired embodiment, the comonomers are a mixture formed of at least two of the above hydrophilic monomers. Alternatively, the comonomers are a mixture formed of at least one hydrophilic monomer and at least one hydrophobic monomer.

In a currently preferred embodiment, a preferred hydrophilic monomer is 2-hydroxyethyl methacrylate (HEMA). By the term "HEMA unit(s)" is meant the structure.

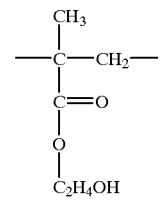

recurring in the polymer obtained by polymerizing hydrophilic material containing 2-hydroxyethyl methacrylate ("HEMA"). Currently preferred comonomers useful in the invention include HEMA and N,N'-dimethylacrylamide or HEMA and methacrylic acid. Still other suitable monomers and comonomers may be readily selected from among those known in the art.

Useful crosslinking agents which can be included in the polymerizable reaction medium include, for example, the polyethylenically unsaturated compounds having at least two polymerizable ethylenic sites, such as the di-, tri- and tetra-ethylenically unsaturated compounds, in particular, the tri-unsaturated crosslinking agents with/without the di-unsaturated crosslinking compounds, for example, divinylbenzene, ethylene glycol dimethacrylate and diacrylate, propylene glycol dimethacrylate and diacrylate, and the di-, tri- and tetra-acrylate or methacrylate esters of the following polyols; triethanolamine, glycerol, pentaerythritol, 1,1,1,-trimethylolpropane; and others. Other suitable crosslinking agents may be readily selected by one of skill in the art.

The diffusion enhancers useful in the invention are mixed with the polymerizable materials, and preferably are uniformly distributed or dispersed (e.g., by mixing, spinning, etc.) in the reaction medium, but do not themselves polymerize. Rather, following the polymerization reaction, pores containing these diffusion enhancers are formed within the polymerized hydrogel material. Thus, the diffusion enhancers are liquids at room and/or body temperatures both prior to and following the polymerization reaction. These compounds include methyl alcohol, allyl alcohol, tetrahydrofurfuryl alcohol, cyclohexyl alcohol; diethylene glycol; polyethylene glycols, glycerol, acetone, ethylene glycol monomethyl ether, ethylene glycol monoethyl ether, ethylene glycol monobutyl ether, glyceryl isopropylidene ether dioxane; tetrahydrofuran; ethyl acetate; dimethyl sulfoxide, and water. Other diffusion enhancers may be selected from those of skill in the art, particularly from among those compounds which are miscible with the starting monomers and are soluble in water.

Advantageously, and in contrast to problems observed by the inventors with prior art pore-formers, the diffusion enhancers described herein do not interfere with homogeneity during spin casting, and thus permit the formation of more homogenous hydrogels than those described in the art.

These advantages are particularly apparent when spin or rotational casting is used to prepare the articles of the invention.

The Polymerization Reaction

In accordance with the method of the invention, a polymerizable mixture is formed by mixing the comonomers described above with a crosslinker and a diffusion enhancer. Suitably, about 50% to about 95%, about 60% to about 90%, or about 75% to about 85%, by weight, of the polymerizable monomers is included in the mixture. Generally, the crosslinker is added in an amount in the range of about 0.1% to about 5%, about 0.5% to about 3%, and about 1%, by weight, of the mixture. The diffusion enhancers are generally included in an amount of about 1% to about 50%, about 5% to about 40%, about 10% to about 30%, or about 20%, by weight, of the mixture.

Preferably the polymerization reaction is conducted in a polymerization column such as a suitable hollow tube fabricated of various materials such as plastics, e.g., polyethylene, polypropylene, and polystyrene; glass; and the like. Cross-sectional areas of the interior of the column are circular in shape and of equal diameter. In preferred embodiments, the column is fabricated from a material that will not significantly impede the transmission of radiation into the polymerization zone of the column. Glass, such as Pyrex, is a preferred material for the polymerization column when using radiation with/without initiation(s) and/or other catalyst(s).

The polymerization reaction can be carried out in bulk or with an inert solvent. Suitable solvents include water; organic solvents such as water-soluble lower aliphatic monohydric alcohols as well as polyhydric alcohols, e.g., glycol, glycerine, dioxane, etc., and mixtures thereof.

Compounds useful in the catalysis of the polymerizable ethylenically unsaturated compounds include the free-radical compounds and/or initiators of the type commonly used in vinyl polymerization such as the organic peroxides, percarbonates, hydrogen peroxides, and alkali metal sulfates, illustrative examples include cumene hydroperoxide, 5-butyl hydroperoxide, benzoyl peroxide, bis(4-t-butylcyclohexyl) peroxydicarbonate, hydrogen peroxide, 2,4-dichlorobenzoyl peroxide, acetyl peroxide, di-n-propyl peroxydicarbonate, di-t-butyl peroxide, di-sec-butyl peroxydicarbonate, ammonium sulfate, potassium sulfate, and sodium sulfate. A preferred catalyst is one which is effective at moderately low temperature such as at about 20–80° C., such as tert-butyl peroctoate, benzoyl peroxide, and di-(sec-butyl) peroxydicarbonate.

A conventional redox polymerization catalyst can also be employed. The advantage of redox initiation is that the reaction occurs at reasonable rates at low temperatures, e.g., 0° C. to 50° C. A large number of reductant-oxidant pairs producing free radicals is known in the art. Examples include sodium bisulfate and ammonium persulfate, sodium thiosulfate and potassium persulfate, and the like.

Preferably, polymerization of the ethylenic compounds can be affected using radiation, e.g., ultraviolet (u.v.), x-ray, gamma radiation, microwave, or other well-known forms of radiation. A preferred catalyst for u.v. cure is benzoin methyl ether (BME).

Catalysts and/or initiators and/or radiation are employed in a catalytically effective amount to optimize the polymerization reaction.

The Hydrogel

The xerogel (i.e., a hydrogel prior to hydration) formed from the polymerization of the reaction mixture described above is a solid at room and/or body temperature, forming a cross-linked matrix. When exposed to an aqueous media, the xerogel will absorb the aqueous fluid and become a hydrogel containing pores which are relatively evenly dispersed throughout the hydrogel matrix. Suitably, the pores formed in the hydrogel range in size from 10 Angstroms ($1 \times 10^{-9}$) to several microns. Other suitable ranges include from 50 Angstroms to 0.1 microns and from 0.1 microns to 1 micron. When the molecule for delivery is a macromolecule, the pore size is suitably over 50 Angstroms. As described herein, the pores contain diffusion enhancers.

The hydrogel does not dissolve upon exposure to water, but permits the imbibing of water. When a hydrogel attains it maximum level of hydration, the water content of the hydrogel is referred to as "equilibrium water content" (EWC). The percent water content of the hydrogel (any state of hydration) is determined as follows:

$$\% \ EWC = \frac{(\text{Weight of hydrogel} - \text{Weight Dry Polymer (Xerogel)})}{(\text{Weight of hydrogel})} \times 100$$

Suitably, a hydrogel of the invention has an EWC value in the range of from about 20% to about 90%, about 35% to about 85%, or about 50% to about 80%, as desired. Advantageously, the hydrogels of the invention have an increased EWC value, as compared to the equivalent hydrogels without diffusion enhancers. Such improvements in EWC value correspond with an increase in release rate.

It is the ability of the hydrogel to swell with water, and thus, increase the area between the cross-links, which permits the passage of active agents. By controlling the level of hydration, it is possible to control the rate of passage of these active agents through the hydrogel matrix into the surrounding environment, e.g., the body. The inventors have found that the use of the diffusion enhancers as described herein facilitates passages of macromolecular active agents. More particularly, during hydration of the hydrogel, the diffusion enhancers leach out of the hydrogel into the surrounding environment, thus permitting the pores to fill with water from the surrounding environment. The presence of the diffusion enhancers described herein, permits the formation of pores, which are larger than those found in their absence. Currently, particularly desired diffusion enhancers include saline, isotonic water, and phosphate buffered saline. These pores provide larger spaces which permit the passage of macromolecular active agents into the surrounding environment. Advantageously, the hydrogels are non-toxic, and once hydrated contain no residual monomers or extractables. Further, the hydrogels are characterized by low reactivity, and are sufficiently flexible that they mimic the surrounding tissue. Thus, these hydrogels are well suited for use in the animal, particularly, mammalian and more particularly, human body.

Thus, in a currently preferred embodiment, the hydrogels of the invention are used in the production of drug delivery devices.

Drug Release Devices

The drug release devices of the invention are suitable for release of large native or recombinant bioactive proteins including, but not limited to, growth factors, interferons, interleukins, granulocyte macrophage colony stimulating factor (GM-CSF), neurotrophic factors and the like. These devices are also suitable for release of smaller molecules, including biological and chemical compounds, and may be readily adapted to delivery of combinations of the various types of proteins and compounds described above.

The amount of active agent employed in the drug delivery devices of the invention will depend not only on the desired daily dose but also on the number of days that dose level is to be maintained. While this amount can be calculated empirically, the actual dose delivered is also a function of any interaction with materials and the carrier, if employed in the device.

In various embodiments, the novel drug delivery device may contain a pharmaceutically acceptable carrier which may be in the form of suspending media, solvents, aqueous systems, and solid substrates or matrices.

Suspending media and solvents useful as the carrier include, for example, oils such as silicone oil (particularly medical grade), corn oil, castor oil, peanut oil and sesame oil; condensation products of castor oil and ethylene oxide combining about 30 to 35 moles of ethylene oxide per mole of castor oil; liquid glyceryl triesters of a lower molecular weight fatty acid; lower alkanols; glycols; polyalkylene glycols.

The aqueous systems include, for example, sterile water, saline, dextrose, dextrose in water or saline, and the like. The presence of electrolytes in the aqueous systems may tend to lower the solubility of the macro-molecular drug in them.

The solid substrates or matrices include, for example starch, gelatin, sugars (e.g. glucose), natural gums (e.g. acacia, sodium alginate, carboxymethyl cellulose), and the like. The carrier may also contain adjuvants such as preserving, stabilizing, wetting and emulsifying agents, and the like.

The hydrating liquid useful in the practice of the invention is typically a liquid simulating the environment in which the active compound will be released, e.g., body fluid, sterile water, tear fluid, physiological saline solution, phosphate buffer solution, and the like. While liquids other than water are useful as the hydrating liquid, the degree to which a hydrophilic membrane is hydrated is referred to as its "water content".

The devices of the invention(s) result in sustained release of the macromolecular drugs over extended periods of time. This time period may range from several days to a few years, for example, from one week to 3 years depending on the desired administration regimen. Preferably, the release time will be about 1 week to 18 months, and longer, it being understood that this time factor is a variable depending on the rate-releasing membrane of choice, its interconnecting pore structure, the active compound of choice, the solubility of the active compound in the liquid medium, and other considerations well known to those skilled in the art.

Methods for determining the release profile (i.e., delay time, release rate and duration) of a macromolecular composition from the delivery device of the invention are well known, and include use of the Fick's First Law of Diffusion. See, e.g., U.S. Pat. No. 5,266,325, which is incorporated herein by reference.

The novel drug delivery devices, in a preferred aspect, are highly useful in the delayed/sustained and the immediate/sustained release of active agents to animals, e.g., humans, sheep dogs, cats, turkeys, cattle, etc. "Delayed/sustained release" is defined as delaying the release of an active agent until after placement in a delivery environment, followed by a sustained, preferably zero-order, release of the agent at a later time. "Immediate/sustained release" is defined as the commencement of the release of an active agent immediately or soon thereafter after placement in a delivery environment, followed by sustained release of the active agent. Other applications of the present invention include controlled delivery in industrial, agricultural and domestic settings.

In preferred aspects, the drug delivery devices of the invention are small cylindrically shaped implants containing within their core an active agent such as a macromolecular composition discussed herein, and optionally, a pharmaceutically acceptable carrier.

One aspect of the invention relates to a delivery device capable of delayed/sustained release of therapeutic dosages of an active agent into an aqueous delivery environment.

The macromolecular compositions of this invention will be present in the delayed/sustained release compositions in varying amounts, depending upon the effect desired.

In a currently preferred embodiment, a vesicle, such as a cartridge, is prepared in which the hydrogels of the invention form the walls of a cavity which contain the active agent. A predetermined amount of an active compound per se or as an admixture with an inert, non-toxic material or as a suspension in a non-toxic material or as a suspension in a non-toxic medium, e.g., medical grade silicone oil, is introduced into the cavity to partially fill the core. The void in the core is thereafter sealed to prevent leakage into or out of the vesicle. Preferably this can be accomplished by introducing sufficient polymerizable material into the void to cover the layer of inert material or to substantially or completely fill the void and thereafter effecting a polymerization reaction to form a plug of water-swellable, water-insoluble polymer which seals the opening of the vesicle. The hydrophilic polymer plug, upon maximum hydration, will have an equilibrium water content value of the hydrophilic vesicle. Using polymerizable material comprising ethylenically unsaturated monomer(s) and desirably crosslinking agent(s), a polymer plug grafted to the inner surface of the vesicle can be obtained.

In a currently desired embodiment, hydrophilic cartridges are prepared by the rotational casting of polymerizable material in a tubular mold, as described in U.S. Pat. Nos. 5,266,325 and 5,292,515, which are incorporated herein by reference. Briefly, the internal radius of the tube is approximately 1.2–1.3 mm, and may be larger. The tube is rotated about its longitudinal axis which is maintained parallel to the ground. Rotational speeds are of the order of 2150 rpm, though greater or lesser speeds could be used, e.g., 1000 rpm or less to 3000 rpm and more. The tubes are fabricated of polyethylene, polypropylene, glass, or other suitable materials. When the polymerizable mixture within the spinning tube stabilizes to the predetermined shape, U.V. light at a distance of less than one foot is then directed at the spinning tube for several minutes, e.g., about 7 minutes, to polymerize the mixture to the shaped product. The shaped product is cured and annealed as follows:

Thermal Cure: 60 minutes at 65° C.

Postcure: 30 minutes at 95° C.

Annealing: 30 minutes at 115° C. with gradual cooling to about 25° C.

After shaping and polishing the closed end of the cartridge to a oval-like cylindrical profile, there is obtained small cylindrically-shaped objects having smooth, unscored cylindrical surfaces. The dimensions of the cartridges are as follows: internal radius 0.98 mm; external radius 1.3 mm; length 25 mm.

In preferred embodiments, small drug delivery devices can be implanted subcutaneously in a human or other animal by perforation. Such devices are characterized by a length of 10–50 mm, or less (e.g., 6–9 mm), an external diameter of 2–5 mm, or less (e.g., 1.5–1.9 mm). The dimensions of the cartridge can vary outside of the limits stated above depending, in particular, on the medical application involved. Animals such as sheep, cows, goats, cattle, and large animals, in general, can tolerate implantation by perforation of larger dimensional drug delivery devices. Implantation can be effected by other means, e.g., open surgery.

Smooth, unscored cylindrically-shaped objects of various lengths, e.g., up to 25 cm and longer, can also be prepared in accordance with the teachings herein. Such objects, in a hydrated state or plasticized with a non-toxic, biocompatible material, can be formed into desired shapes. A ring shape, for use as pessaries, surgical implants, etc. Yet other drug delivery devices may be prepared using techniques known to those of skill in the art.

The following examples are provided to illustrate the invention and do not limit the scope thereof. One skilled in the art will appreciate that although specific reagents and conditions are outlined in the following examples, modifications can be made which are meant to be encompassed by the spirit and scope of the invention.

EXAMPLE 1

Monomeric mixture comprised of 94.5% 2-HEMA, 5% propylene glycol and 0.5% ethylene glycol dimethacrylate (EGDMA) was prepared. 2-HEMA was previously purified by vacuum distillation. To the resulting mixture, 0.2% benzoin methyl ether was added and dissolved.

An implant cartridge was prepared essentially as described in U.S. Pat. No. 5,266,325. More particularly, the mixture was deoxygenated by bubbling nitrogen through it for 10 minutes. To avoid premature polymerization the mixture was shielded from light. One end of a polypropylene tube (65 mm in length and $d_i$ of 2.5 mm) was plugged with a silicone sealant; the other end of the tube was sealed with a plug made by injecting a small amount of the above mixture, which was cured under a UV lamp for 5 minutes. Using a syringe filled with said mixture, the silicone plug was punctured and the tube was filled with the mixture to a height of about 10 mm from the top. The tube was inserted in a lathe collet and spun (spinning axis parallel to the ground) at about 2200 rpm. The centrifugal force created by the spinning tube caused the radially outward displacement of the mixture to assume a predetermined hollow cylindrical liquid configuration (i.e., a hollow tube of polymerizable liquid mixture). The spinning tube was then exposed to UV light for 7 minutes to polymerize the "liquid tube" to a solid hydrophilic tube (cartridge). The cartridge within the polypropylene tube was postcured for 14 hours at 65° C., followed with an additional 40 minutes at 105° C., and annealed at 116° C. for 40 minutes, and then slowly cooled to 22° C.

The cartridge was ejected from the tube, inspected for defects, and cut to a length of 30 mm. There was obtained a precisely dimensional plastic cartridge fabricated of crosslinked homogeneous 94.5% HEMA/5% polypropylene glycol/0.5% EDGMA polymer characterized by recurring hydrophilic units. The weight of the cartridge was recorded.

This cartridge is available for filling with an active agent by tightly packing it to a 20 mm height. The filled cartridge is weighed again to determine the weight of active agent. The empty space of the cartridge is filled with the aforesaid monomeric mixture. Part of the cartridge containing the active agent is covered with aluminum foil. The cartridge is then placed in the lathe and spun slowly (spinning axis of cartridge parallel to ground) under a UV lamp for 5 minutes to effect polymerization of the mixture. Postcuring of the polymer plug was effected by maintaining the cartridge at 50° C. for 18 hours. The end product is a drug delivery device.

EXAMPLE 2

Monomeric mixture comprised of 92.5% 2-HEMA, 2% methacrylic acid, 5% polyethylene glycol 200 and 0.5% ethylene glycol dimethacrylate was prepared and processed as in example 1.

EXAMPLE 3

Monomeric mixture comprised of 74.5% 2-HEMA, 20% N,N'-dimethylacrylamide (N,N'-DMA), 5% isopropyl alcohol and 0.5% ethylene glycol dimethacrylate was prepared and processed as in example 1.

EXAMPLES 4–6

Monomeric mixtures comprised of 2-HEMA and propylene glycol in the ratios shown in the Table were prepared and processed as in example 1. (The concentrations of crosslinker and catalyst remained constant.)

TABLE

| Example | % HEMA | % Propylene Glycol |
|---------|--------|--------------------|
| 4 | 89.5 | 10 |
| 5 | 84.5 | 15 |
| 6 | 79.5 | 20 |

EXAMPLES 7–9

Monomeric mixtures comprised of 2-HEMA, methacrylic acid and polyethylene glycol 200 (PEG 200) in the ratios shown in the Table below were prepared and processed as in example 1. (Crosslinker and catalyst levels remained constant.)

TABLE

| Example | % HEMA | % MA | % PEG 200 |
|---------|--------|------|-----------|
| 7 | 87.5 | 2.0 | 10.0 |
| 8 | 82.5 | 2.0 | 15.0 |
| 9 | 77.5 | 2.0 | 20.0 |

EXAMPLES 10–12

Monomeric mixtures comprised of 2-HEMA, N,N'-DMA and isopropyl alcohol (IPA) in the ratios shown in the Table below were prepared and processed as in example 1. (Crosslinker and catalyst levels remained constant.)

TABLE

| Example | % HEMA | % N,N'-DMA | % IPA |
|---------|--------|------------|-------|
| 10 | 69.5 | 20.0 | 10.0 |
| 11 | 64.5 | 20.0 | 15.0 |
| 12 | 59.5 | 20.0 | 20.0 |

All of the above examples can be also catalyzed by thermal free-radical catalysts, such as benzoyl peroxide, in place of the UV initiator, such as benzoin methyl ether (BME). Such suitable catalysts are listed, for example, in U.S. Pat. No. 5,266,325. In this case, the UV lamp used in conjunction with the UV initiator, i.e., BME, will be replaced by a heat lamp, or the spinning portion of the spin casting apparatus may be incased within a heating column.

EXAMPLE 13

A conventional redox polymerization is employed in this example, where the diffusion enhancer is water.

The monomeric mixture is composed of 86.5% 2-HEMA, 3% methacrylic acid, 10% water and 0.5% trimethylol propane trimethacrylate. The water contains the redox system, which includes 0.14% by weight of each sodium metabisulfate and ammonium persulfate based on the amount of water.

The mixture is then purged, injected into the mold and spun at 2000 RPM for 15 minutes at ambient temperature. Application of heat will increase the rate of polymerization. Post-curing is effected by allowing the cartridges to remain in the molds overnight at 37° C.

EXAMPLE 14

Polymers and drug release devices made from three of the listed examples were evaluated.

Hydrogels from examples 6, 9 and 12 were used to demonstrate the effect of the diffusion enhancers on the polymer properties. Since the increase in the hydrogel pore size due to the enhancers will result in an increase in the degree of hydration of the hydrogel, the equilibrium water contents (EWC) of polymers prepared according to the invention (i.e., with diffusion enhancers) were compared with the equivalent polymers lacking diffusion enhancers. The results shown in the table below illustrate that the effect on water contents can be in some cases quite dramatic.

TABLE

Effect of the Diffusion Enhancer on Polymer EWC
% EQUILIBRIUM WATER CONTENT (EWC)

| EXAMPLE | NON-MODIFIED POLYMER | MODIFIED POLYMER |
|---|---|---|
| 6 | 36.8 | 37.0 |
| 9 | 57.2 | 60.0 |
| 12 | 55.7 | 65.2 |

The polymers from the examples 6, 9 and 12 were also used to fabricate subcutaneous drug release devices for the release of Lysozyme (a protein of molecular weight 14.6 kD which is often used as a model for testing of delivery devices) [#L 6876, Sigma-Aldrich Co]. Again, both modified and non-modified polymers were used and the release rates evaluated. FIGS. 1 (Example 9) and 2 (Example 12) show that up to 30 fold increase in the release rates of Lysozyme can be achieved from devices modified with diffusion enhancers as compared to their non-modified polymer equivalents.

Of the tested diffusion enhancing agents, the isopropyl alcohol (Example 12) shown to be most effective in terms of the increase in equilibrium water content and the corresponding improvement in release rates (as evaluated with Lysozyme). Propylene glycol was shown to be least effective (example 6) in elevating the EWC (37% vs. 36.8%) and improving the release characteristics of Lysozyme (the release rates were <0.5 µg/day in both cases).

Another demonstration of the effectiveness of these modifiers in enhancing the release of large molecules was the observed effect of osmotic pressure. In the case of implants made without the diffusion enhancers, the Lysozyme implants became inflated due to the internal increase in osmotic pressure resulting, in some cases, in destruction (burst) of the implant. This was not observed in the modified implants, which indicates that equilibrium release kinetics were reached and the osmotic pressure was equalized.

All publications cited in this specification are incorporated herein by reference herein. While the invention has been described with reference to a particularly preferred embodiment, it will be appreciated that modifications can be made without departing from the spirit of the invention. Such modifications are intended to fall within the scope of the appended claims.

What is claimed is:

1. A method for preparing a homogenous porous hydrogel for sustained delivery of drugs, said method comprising the steps of:
    (a) forming a polymerizable liquid mixture containing about 60 weight percent to about 95 weight percent polymerizable comonomers, wherein at least one of the comonomers is hydrophilic, and sufficient amounts of a crosslinker and a liquid diffusion enhancer which is miscible with the comonomers, to yield a homogenous porous copolymer having the equilibrium water content (EWC) value in the range from about 20% to about 85%;
    wherein the polymerizable liquid mixture contains about 1 weight percent to about 50 weight percent diffusion enhancer selected from the group consisting of tetrahydrofurfuryl alcohol, cyclohexyl alcohol, acetone, ethylene glycol monomethyl ether, ethylene glycol monoethyl ether, ethylene glycol monobutyl ether, glyceryl isopropylidene ether dioxane, tetrahydrofuran, ethyl acetate, and dimethyl sulfoxide; and
    (b) forming a hydrogel useful for sustained release of macromolecules consisting of the homogenous porous copolymer.

2. The method according to claim 1, wherein the comonomers comprise at least one monomer selected from the group consisting of 2-hydroxyethyl methacrylate (HEMA), N,N'-dimethylacrylamide, methacrylic acid, acrylic acid, N-isopropylacrylamide, vinyl pyrrolidine, hydroxypropyl methacrylate, and acrylates.

3. The method according to claim 1, wherein the polymerizable liquid mixture yields a homogenous copolymer having an EWC value in the range from about 75% to 85%.

4. The method according to claim 1, wherein said article is formed by spin casting.

5. The method according to claim 1, wherein the polymerizable liquid mixture contains about 0.1 weight percent to about 5 weight percent of a crosslinker.

6. The method according to claim 5, wherein said crosslinker is selected from the group consisting of ethylene glycol dimethacrylate and trimethylol propane trimethacrylate.

7. The method according to claim 1, wherein said polymerizable liquid mixture further comprises an ultraviolet initiator.

8. The method according to claim 7, wherein the ultraviolet initiator is benzoin methyl ether.

9. The method according to claim 1, wherein said polymerizable liquid mixture further comprises reductant-oxidant polymerization catalyst pairs.

10. The method according to claim 9, wherein said reductant-oxidant pairs are selected from the group consisting of (a) sodium and ammonium persulfate and (b) sodium and potassium persulfate.

11. An article produced according to the method of claim 1.

12. A method for the preparation of a delivery device for the sustained release of an active agent therefrom which comprises:
    (a) introducing active agent, and optionally, a pharmaceutically acceptable carrier, into the reservoir of the hydrogel prepared according to claim 1, in an amount sufficient to provide extended sustained release of the active agent;

(b) introducing at least one polymerizable liquid monomer into the upper portion of the reservoir in an amount to fill the reservoir, said liquid monomer having an equilibrium water content value in its polymerized state which exceeds the equilibrium water content value of the cartridge; and (c) polymerizing said monomer to seal the opening of the reservoir with a plug of water-swellable, water-insoluble polymer to form a delivery device which provides a predetermined release of the active agent.

13. A delivery device produced according to the method of claim 12.

14. A method for preparing a homogenous porous hydrogel article for sustained delivery of drugs, said method comprising the steps of:

(a) forming a polymerizable liquid mixture containing about 60 weight percent to about 95 weight percent comonomers comprising 2-hydroxyethyl methacrylate (HEMA), about 10 to about 50 weight percent of a liquid diffusion enhancer which is miscible with the comonomers, and a crosslinker;

(b) polymerizing the polymerizable liquid mixture into a xerogel which upon exposure to water forms a hydrogel consisting of a homogenous copolymer having pores spaced regularly throughout, wherein said pores are each about 10 Angstroms to about 1.0 microns in diameter and contain the liquid diffusion enhancer, said hydrogel having the equilibrium water content (EWC) value in the range from about 35% to about 85%, wherein said hydrogel is in the form of a cartridge having walls of uniform thickness which define a reservoir, wherein said article is useful for sustained release of macromolecules having a molecular weight of up to 100,000.

15. The method according to claim 14, wherein said polymerizable liquid mixture contains about 80 weight percent to about 95 weight percent comonomers.

16. The method according to claim 14, wherein the comonomers further comprise a comonomer selected from the group consisting of methacrylic acid and N-N'-dimethylacrylamide.

17. The method according to claim 14, wherein the diffusion enhancer is present in an amount of about 20 weight percent to about 40 weight percent.

18. An article produced according to the method of claim 14.

19. A method for the preparation of a delivery device for the sustained release of an active agent therefrom which comprises:

(a) introducing active agent, and optionally, a pharmaceutically acceptable carrier, into the reservoir of the hydrogel prepared according to claim 14, in an amount sufficient to provide extended sustained release of the active agent;

(b) introducing at least one polymerizable liquid monomer into the upper portion of the reservoir in an amount to fill the reservoir, said liquid monomer having an equilibrium water content value in its polymerized state which exceeds the equilibrium water content value of the cartridge; and (c) polymerizing said monomer to seal the opening of the reservoir with a plug of water-swellable, water-insoluble polymer to form a delivery device which provides a predetermined release of the active agent.

20. A delivery device produced according to the method of claim 19.

21. The method according to claim 14, wherein said polymerizable liquid mixture contains about 60 weight percent HEMA, about 20 weight percent dimethylacrylamide, and a diffusion enhancer comprising about 20 weight percent isopropyl alcohol.

22. The method according to claim 14, wherein said polymerizable liquid mixture contains about 77 weight percent HEMA, about 2 weight percent methylacrylamide, and about 20% polyethylene glycol.

23. The method according to claim 14, wherein said polymerizable liquid mixture contains about 80 weight percent HEMA and a diffusion enhancer comprising about 20 weight percent polyethylene glycol.

24. A hydrogel comprising a homogeneous copolymer matrix having pores spaced regularly throughout the matrix, wherein said pores are each about 10 Angstroms to about 1.0 microns in diameter and contain a liquid diffusion enhancer, said liquid diffusion enhancer consisting of about 10 to about 50% by weight of the total weight of the hydrogel prior to exposure to water, wherein said hydrogel has an equilibrium water content (EWC) in the range of about 35% to about 85%.

25. The hydrogel according to claim 24, wherein the diffusion enhancer is present in an amount of about 10% to about 20% by weight.

26. The hydrogel according to claim 24, wherein said copolymer matrix comprises about 60% 2-hydroxyethylmethacrylate (HEMA) by weight of the total weight of the hydrogel prior to exposure to water, said liquid diffusion enhancer consisting of about 20% by weight of the total weight of the hydrogel prior to exposure to water, wherein said hydrogel has an equilibrium water content (EWC) in the range of about 35% to about 85%.

* * * * *